(12) United States Patent
Moeckel et al.

(10) Patent No.: US 6,812,006 B2
(45) Date of Patent: Nov. 2, 2004

(54) NUCLEOTIDE SEQUENCES WHICH CODE FOR THE LYSR3 GENE

(75) Inventors: Bettina Moeckel, Duesseldorf (DE); Caroline Kreutzer, Melle (DE)

(73) Assignee: Degussa AG, Hanau-Wolfgang (DE)

( * ) Notice: Subject to any disclaimer, the term of this patent is extended or adjusted under 35 U.S.C. 154(b) by 0 days.

(21) Appl. No.: 09/867,537

(22) Filed: Dec. 11, 2001

(65) Prior Publication Data

US 2003/0100099 A1 May 29, 2003

(30) Foreign Application Priority Data

Aug. 10, 2000 (DE) .......................................... 100 39 049

(51) Int. Cl.⁷ ................................................ C12P 13/04
(52) U.S. Cl. ............... 435/106; 435/252.3; 435/252.32; 435/320.1; 530/350; 536/23.1
(58) Field of Search .............................. 435/106, 252.3, 435/252.32, 320.1; 530/350; 536/23.1

(56) References Cited

FOREIGN PATENT DOCUMENTS

| EP | 1108790 A2 | 6/2001 |
|----|-----------|--------|
| WO | WO 99/18228 | 4/1999 |
| WO | WO 01/00802 | 1/2001 |
| WO | WO 01/00842 | 1/2001 |
| WO | WO 01/00845 | 1/2001 |
| WO | WO 01/00847 | 1/2001 |

OTHER PUBLICATIONS

M. Vrljic, et al., Molecular Microbiology, vol. 22, No. 5, pps. 815–826, "A New Type of Transporter with a New Type of Cellular Function: ι–Lysine Export from Corynebacterium Glutamicum," 1996.

B. J. Eikmanns, et al., Antonie Van Leeuwenhoek, vol. 46, pps. 145–163, "Molecular Aspects of Lysine, Threonine, and Isoleucine Biosynthesis in Corynebacterium Glutamicum," 1993.

*Primary Examiner*—Ponnathapu Achutamurthy
*Assistant Examiner*—Christian L. Fronda
(74) *Attorney, Agent, or Firm*—Oblon, Spivak, McClelland, Maier & Neustadt, P.C.

(57) ABSTRACT

The present invention relates to polynucleotides corresponding to the lysR3 gene and which encode a LysR3 transcriptional regulator, methods of producing L-amino acids, and methods of screening for polynucleotides which encode proteins having LysR3 transcriptional regulator activity.

12 Claims, 1 Drawing Sheet

Figure 1: Plasmid map of pCR2.1lysR3int ic Application No. DE 10039049.8 filed Aug. 10, 2000, the entire contents of which are incorporated herein by reference.

SEQUENCE LISTING

<160> NUMBER OF SEQ ID NOS: 5

<210> SEQ ID NO 1
<211> LENGTH: 1032
<212> TYPE: DNA
<213> ORGANISM: Corynebacterium glutamicum
<220> FEATURE:
<221> NAME/KEY: CDS
<222> LOCATION: (201)..(830)

<400> SEQUENCE: 1

```
gatgatcaaa tacttctaga tgtcatcgat aatgggcagg gatttgatgt ggcagaagtg      60
atccgtaaaa aatccattgg actgcccaca gcgcaacgcc gggctgaagg gctgggcgga     120
acaataatta ttgaatctac aatcggatcg ggaactggaa tttccgcccg ttttccctat     180
ccacaaaagg accaagataa gtg atc cgt att ctg ttg gct gat gat cat ccc    233
                       Val Ile Arg Ile Leu Leu Ala Asp Asp His Pro
                         1               5                  10 gtt gtt cgc gca ggc ctt gcc tcc ttg ctg gtg agt gaa gat gat ttt        281
Val Val Arg Ala Gly Leu Ala Ser Leu Leu Val Ser Glu Asp Asp Phe
             15                  20                  25 gag ata gtg gac atg gtg ggc acc cca gat gat gcc gtt gcg cgc gcc        329
Glu Ile Val Asp Met Val Gly Thr Pro Asp Asp Ala Val Ala Arg Ala
         30                  35                  40 gcg gaa ggc ggg gtg gat gtg gtg ttg atg gat ctg cgt ttt ggt gat        377
Ala Glu Gly Gly Val Asp Val Val Leu Met Asp Leu Arg Phe Gly Asp
     45                  50                  55 caa cca ggc atc gag gtc gcc ggc ggg gta gag gca acg cgt cgc atc        425
Gln Pro Gly Ile Glu Val Ala Gly Gly Val Glu Ala Thr Arg Arg Ile
 60                  65                  70                  75 cgt gcg ctg gac aac ccg cca cag gta ctg gtg gtg acc aac tac tcc        473
Arg Ala Leu Asp Asn Pro Pro Gln Val Leu Val Val Thr Asn Tyr Ser
                 80                  85                  90 aca gac ggc gat gtg gtg ggc gca gta tct gct ggt gcc gtg ggg tat        521
Thr Asp Gly Asp Val Val Gly Ala Val Ser Ala Gly Ala Val Gly Tyr
             95                 100                 105
```

```
ttg ctc aaa gat agc tcc cca gaa gat ctc att gcc ggt gtt cgc gat      569
Leu Leu Lys Asp Ser Ser Pro Glu Asp Leu Ile Ala Gly Val Arg Asp
        110                 115                 120 gcc gcg cgg gga gaa tca gtg ctt tca aag cag gtc gcc agc aag atc      617
Ala Ala Arg Gly Glu Ser Val Leu Ser Lys Gln Val Ala Ser Lys Ile
    125                 130                 135 atg ggg cgg atg aac aac ccc atg act gct ctc agt gcc aga gaa att      665
Met Gly Arg Met Asn Asn Pro Met Thr Ala Leu Ser Ala Arg Glu Ile
140                 145                 150                 155 gaa gtg ctg tcc ttg gtg gcg caa ggg caa agc aat aga gaa atc ggc      713
Glu Val Leu Ser Leu Val Ala Gln Gly Gln Ser Asn Arg Glu Ile Gly
                160                 165                 170 aag aaa ctt ttc ctc act gag gcc acg gtg aaa agt cac atg ggg cat      761
Lys Lys Leu Phe Leu Thr Glu Ala Thr Val Lys Ser His Met Gly His
            175                 180                 185 gtg ttc aac aag ctg gat gtc acc tct aga aca gct gcg gta gct gaa      809
Val Phe Asn Lys Leu Asp Val Thr Ser Arg Thr Ala Ala Val Ala Glu
        190                 195                 200 gcc aga cag cgc gga att atc tagacgcaca cgtgttggta accgatcaca         860
Ala Arg Gln Arg Gly Ile Ile
    205                 210 ccagcgcacg ctgctaatct tcactccatg aacaaggtgc agcgcaggtc actgatggcg    920
ttgtgcatga cggtggcatt tgctggagga agcctgaccg cgtgcacacc tcgtcctgat    980
accgcagacc ccatcgcaga ggaattcctt caagcttggg catcgcaaga tt           1032

<210> SEQ ID NO 2
<211> LENGTH: 210
<212> TYPE: PRT
<213> ORGANISM: Corynebacterium glutamicum

<400> SEQUENCE: 2

Val Ile Arg Ile Leu Leu Ala Asp Asp His Pro Val Val Arg Ala Gly
1               5                   10                  15

Leu Ala Ser Leu Leu Val Ser Glu Asp Asp Phe Glu Ile Val Asp Met
            20                  25                  30

Val Gly Thr Pro Asp Asp Ala Val Ala Arg Ala Ala Glu Gly Gly Val
        35                  40                  45

Asp Val Val Leu Met Asp Leu Arg Phe Gly Asp Gln Pro Gly Ile Glu
    50                  55                  60

Val Ala Gly Gly Val Glu Ala Thr Arg Arg Ile Arg Ala Leu Asp Asn
65                  70                  75                  80

Pro Pro Gln Val Leu Val Val Thr Asn Tyr Ser Thr Asp Gly Asp Val
                85                  90                  95

Val Gly Ala Val Ser Ala Gly Ala Val Gly Tyr Leu Leu Lys Asp Ser
            100                 105                 110

Ser Pro Glu Asp Leu Ile Ala Gly Val Arg Asp Ala Ala Arg Gly Glu
        115                 120                 125

Ser Val Leu Ser Lys Gln Val Ala Ser Lys Ile Met Gly Arg Met Asn
    130                 135                 140

Asn Pro Met Thr Ala Leu Ser Ala Arg Glu Ile Glu Val Leu Ser Leu
145                 150                 155                 160

Val Ala Gln Gly Gln Ser Asn Arg Glu Ile Gly Lys Lys Leu Phe Leu
                165                 170                 175

Thr Glu Ala Thr Val Lys Ser His Met Gly His Val Phe Asn Lys Leu
            180                 185                 190
```

```
Asp Val Thr Ser Arg Thr Ala Ala Val Ala Glu Ala Arg Gln Arg Gly
        195                 200                 205

Ile Ile
    210

<210> SEQ ID NO 3
<211> LENGTH: 323
<212> TYPE: DNA
<213> ORGANISM: Corynebacterium glutamicum

<400> SEQUENCE: 3
gatgtggtgt tgatggatct gcgttttggt gatcaaccag gcatcgaggt cgccggcggg      60
gtagaggcaa cgcgtcgcat ccgtgcgctg gacaacccgc cacaggtact ggtggtgacc     120
aactactcca cagacggcga tgtggtgggc gcagtatctg ctggtgccgt ggggtatttg     180
ctcaaagata gctccccaga agatctcatt gccggtgttc gcgatgccgc gcggggagaa     240
tcagtgcttt caaagcaggt cgccagcaag atcatggggc ggatgaacaa ccccatgact     300
gctctcagtg ccagagaaat tga                                             323

<210> SEQ ID NO 4
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 4
gatgtggtgt tgatggatct                                                  20

<210> SEQ ID NO 5
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 5
tcaatttctc tggcactgag                                                  20
```

NUCLEOTIDE SEQUENCES WHICH CODE FOR THE LYSR3 GENE

CROSS-REFERENCE TO RELATED APPLICATION

The present application claims priority to German Application No. DE 10039049.8 filed Aug. 10, 2000, the entire contents of which are incorporated herein by reference.

BACKGROUND OF THE INVENTION

1. Field of the Invention

The invention provides nucleotide sequences from *Coryneform* bacteria which code for the lysR3 gene and a process for the fermentative preparation of amino acids, in particular L-lysine and L-valine, by attenuation of the lysR3 gene. The lysR3 gene codes for the LysR3 protein, which is a transcription regulator of the LysR family.

2. Discussion of the Background

L-Amino acids, in particular L-lysine and L-valine, are used in human medicine and in the pharmaceuticals industry, in the foodstuffs industry and very particularly in animal nutrition.

It is known that amino acids are prepared by fermentation from strains of *Coryneform* bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the strain of *Corynebacterium* strains which produce L-amino acids.

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that attenuation of lysR3 gene encoding the a LysR3 transcriptional regulation protein would improve L-amino acid yields.

SUMMARY OF THE INVENTION

One object of the present invention, is providing a new process adjuvant for improving the fermentative production of L-amino acids, particularly L-lysine and L-glutamate. Such process adjuvants include enhanced bacteria, preferably enhanced *Coryneform* bacteria which express attenuated amounts of LysR3 transcriptional regulator which is encoded by the lysR3 gene.

Thus, another object of the present invention is providing such an bacterium, which expresses an attenuated amount of LysR3 transcriptional regulator or gene products of the lysR3 gene.

Another object of the present invention is providing a bacterium, preferably a *Coryneform bacterium*, which expresses a polypeptide that has an attenuated LysR3 transcriptional regulator activity. Another object of the invention is to provide a nucleotide sequence encoding a polypeptide which has LysR3 transcriptional regulator sequence. One embodiment of such a sequence is the nucleotide sequence of SEQ ID NO: 1.

A further object of the invention is a method of making LysR3 transcriptional regulator or an isolated polypeptide having a LysR3 transcriptional regulator activity, as well as use of such isolated polypeptides in the production of amino acids. One embodiment of such a polypeptide is the polypeptide having the amino acid sequence of SEQ ID NO: 2.

Other objects of the invention include methods of detecting nucleic acid sequences homologous to SEQ ID NO: 1, particularly nucleic acid sequences encoding polypeptides that have LysR3 transcriptional regulator activity, and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

Where L-amino acids or amino acids are mentioned in the following, this means one or more amino acid, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

When L-lysine or lysine are mentioned in the following, not only the bases but also the salts, such as e.g. lysine monohydrochloride or lysine sulfate, are meant by this.

The invention provides an isolated polynucleotide from coryneform bacteria, comprising a polynucleotide sequence which codes for the lysR3 gene, chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), the polypeptide preferably having the activity of the transcription regulator LysR3.

The invention also provides the above-mentioned polynucleotide, this preferably being a DNA which is capable of replication, comprising:

(i) the nucleotide sequence shown in SEQ ID No.1 or (ii) at least one sequence which corresponds to sequence (i) within the range of the degeneration of the genetic code, or (iii) at least one sequence which hybridizes with the sequences complementary to sequences (i) or (ii), and optionally (iv) sense mutations of neutral function in (i).

The invention also provides:

a DNA which is capable of replication and comprises the nucleotide sequence as shown in SEQ ID No.1;

a polynucleotide which codes for a polypeptide which comprises the amino acid sequence as shown in SEQ ID No. 2;

a vector containing the polynucleotide according to the invention, point d, in particular pCR2.1lysR3int, deposited in *Escherichia coli* DSM 13618 at the DSMZ [German Collection of Microorganisms and Cell Cultures], Braunschweig (Germany);

and *Coryneform* bacteria which contain an insertion or deletion in the lysR3 gene, in particular using the vector pCR2.1lysR3int.

The invention also provides polynucleotides which substantially comprise a polynucleotide sequence, which are obtainable by screening by means of hybridization of a corresponding gene library, which comprises the complete gene with the polynucleotide sequence corresponding to SEQ ID No. 1, with a probe which comprises the sequence of the polynucleotide mentioned, according to SEQ ID No. 1 or a fragment thereof, and isolation of the DNA sequence mentioned.

Polynucleotide sequences according to the invention are suitable as hybridization probes for RNA, cDNA and DNA, in order to isolate, in the full length, nucleic acids or polynucleotides or genes which code for the LysR3 protein or to isolate those nucleic acids or polynucleotides or genes which have a high similarity with the sequence of the lysR3 gene.

Polynucleotide sequences according to the invention are furthermore suitable as primers with the aid of which DNA of genes which code for the LysR3 protein can be prepared with the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the LysR3 protein, and also those which are at least 70%, preferably at least 80% and in particular at least 90% to 95% identical to the polypeptide according to SEQ ID No. 2 and have the activity mentioned.

The invention moreover provides a process for the fermentative preparation of amino acids, in particular L-lysine and L-valine, using *Coryneform* bacteria which in particular already produce amino acids, and in which the nucleotide sequences which code for the lysR3 gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

The microorganisms which the present invention provides can prepare amino acids, in particular L-lysine and L-valine, from glucose, sucrose, lactose, fructose, maltose, molasses, starch, cellulose or from glycerol and ethanol. They can be representatives of *Coryneform* bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 or L-amino acid-producing mutants or strains prepared therefrom, such as, for example, the L-lysine-producing strains

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM 5714 and
*Corynebacterium glutamicum* DSM 12866
or such as, for example, the L-valine-producing strains
*Corynebacterium glutamicum* DSM 12455
*Corynebacterium glutamicum* FERM-P 9325
*Brevibacterium lactofermentum* FERM-P 9324
*Brevibacterium lactofermentum* FERM-BP 1763.

Preferably, a bacterial strain with attenuated expression of a lysR3 gene that encodes a polypeptide with LysR3 transcriptional regulation activity will improve amino acid yield at least 1%.

The inventors have succeeded in isolating the new lysR3 gene of *C. glutamicum* which codes for the LysR3 protein, which is a transcription regulator of the LysR family.

To isolate the lysR3 gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Börmann et al. (Molecular Microbiology 6(3), 317–326) (1992)) in turn describe a gene library of *C. glutamicum* ATCC13032 using the cosmid pHC79 (Hohn and Collins, 1980, Gene 11, 291–298).

To prepare a gene library of *C. glutamicum* in *E. coli* it is also possible to use plasmids such as pBR322 (Bolivar, 1979, Life Sciences, 25, 807–818) or pUC9 (Vieira et al., 1982, Gene, 19:259–268). Suitable host are, in particular, those *E. coli* strains which are restriction- and recombination-defective, such as, for example, the strain DH5α (Jeffrey H. Miller: "A Short Course in Bacterial Genetics, A Laboratory Manual and Handbook for *Escherichia coli* and Related Bacteria", Cold Spring Harbour Laboratory Press, 1992).

The long DNA fragments cloned with the aid of cosmids or other λ-vectors can then be subcloned in turn into the usual vectors suitable for DNA sequencing.

Methods of DNA sequencing are described, inter alia, by Sanger et al. (Proceedings of the National Academy of Sciences of the United States of America USA, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the lysR3 gene and which, as SEQ ID No. 1, is a constituent of the present invention has been found in this manner. The amino acid sequence of the corresponding protein has furthermore been derived from the present DNA sequence by the methods described above. The resulting amino acid sequence of the lysR3 gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology 41: 255–260 (1991)). Instructions for amplification of DNA sequences with the aid of the polymerase chain reaction (PCR) can be found by the expert, inter alia, in the handbook by Gait: Oligonukleotide [sic] synthesis: A Practical Approach (IRL Press, Oxford, UK, 1984) and in Newton and Graham: PCR (Spektrum Akademischer Verlag, Heidelberg, Germany, 1994).

In the work on the present invention, it has been found that *Coryneform* bacteria produce amino acids, in particular L-lysine and L-valine, in an improved manner after attenuation of the lysR3 gene.

To achieve an attenuation, either the expression of the lysR3 gene or the catalytic properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Pátek et al. (Microbiology 142: 1297 (1996)), Vasicova et al. (Journal of Bacteriology 181: 6188 (1999)) and in known textbooks of genetics and molecular biology, such as e.g. the textbook by Knippers ("Molekulare Genetik [Molecular Genetics]", 6th edition, Georg Thieme Verlag, Stuttgart, Germany, 1995) or that by Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus *Corynebacterium glutamicum*: Aufhebung der allosterischen Regulation und Struktur des Enzyms [Threonine dehydratase from *Corynebacterium glutamicum*: Cancelling the allosteric regulation and structure of the enzyme]", Reports from the Jülich Research Centre, Jül-2906, ISSN09442952, Jülich, Germany, 1994). Summarizing descriptions can be found in known textbooks of genetics and molecular biology, such as e.g. that by Hagemann ("Allgemeine Genetik [General Genetics]", Gustav Fischer Verlag, Stuttgart, 1986).

Possible mutations are transitions, transversions, insertions and deletions. Depending on the effect of the amino acid exchange on the enzyme activity, missense mutations or nonsense mutations are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik [Molecular Genetics]", 6th edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986).

A common method of mutating genes of *C. glutamicum* is the method of gene disruption and gene replacement described by Schwarzer and Pühler (Bio/Technology 9, 84–87 (1991)).

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), PGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)) or pEM1 (Schrumpf et al, 1991, Journal of Bacteriology 173:4510–4516). The plasmid vector which contains the central part of the coding region of the gene is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) to eliminate the recA gene of *C. glutamicum*.

Figure 1:
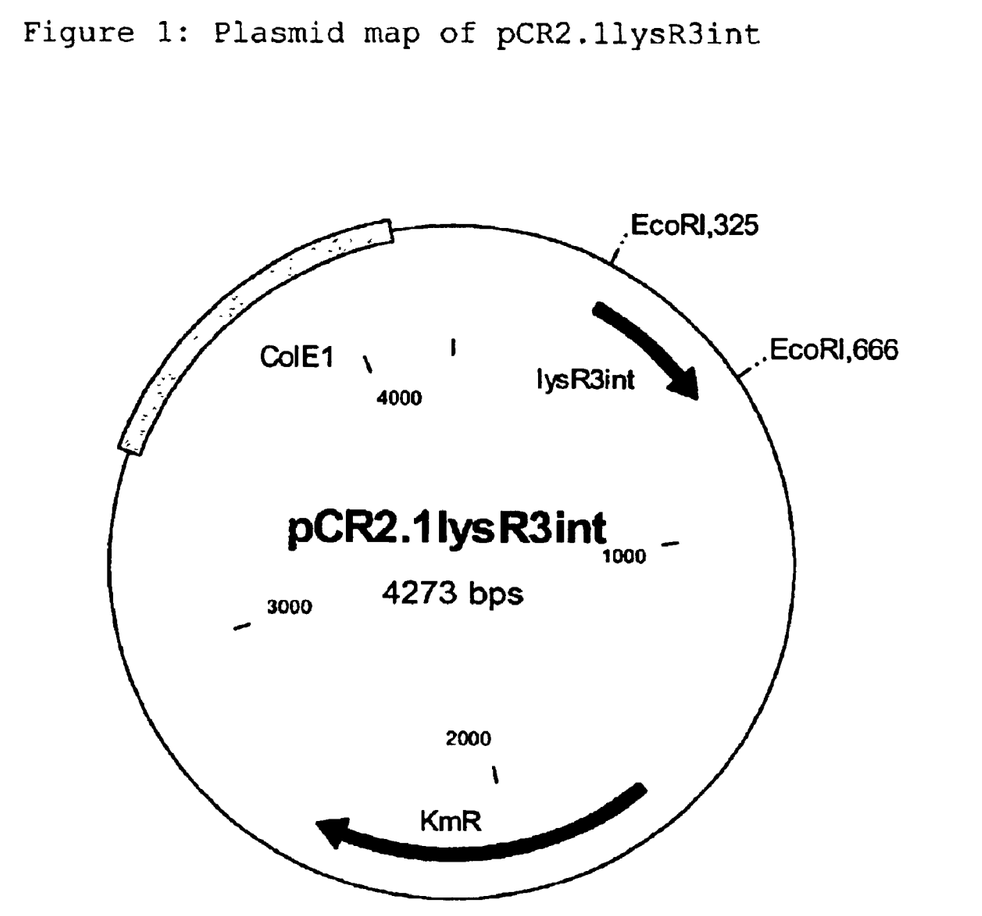
FIG. 1: Map of the plasmid pCR2.1lysR3int.

FIG. 1 shows by way of example the plasmid vector pCR2.1lysR3int, with the aid of which the lysR3 gene can be disrupted or eliminated.

In the method of gene replacement, a mutation, such as e.g. a deletion, insertion or base exchange, is established in vitro in the gene of interest. The allele prepared is in turn cloned in a vector which is not replicative for *C. glutamicum* and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al. (Microbiology 144, 915–927 (1998)) to eliminate the pyc gene of *C. glutamicum* by a deletion.

A deletion, insertion or a base exchange can be incorporated into the lysR3 gene in this manner.

In addition, it may be advantageous for the production of L-amino acids, in particular L-lysine and L-valine, to enhance, in particular to over-express, one or more enzymes of the particular biosynthesis pathway, of glycolysis, of anaplerosis, of the pentose phosphate cycle or of amino acid export, in addition to attenuation of the lysR3 gene.

Thus, for example, for the preparation of L-lysine, at the same time one or more of the genes chosen from the group consisting of the dapA gene which codes for dihydrodipicolinate synthase (EP-B 0 197 335), the eno gene which codes for enolase (DE: 19947791.4), the zwf gene which codes for the zwf gene product (JP-A-09224661), the pyc gene which codes for pyruvate carboxylase (Peters-Wendisch et al.(Microbiology 144, 915–927 (1998))

the lysE gene which codes for lysine export (DE-A-195 48 222)

can be enhanced, in particular over-expressed.

It may furthermore be advantageous for the production of amino acids, in particular L-lysine, in addition to the attenuation of the lysR3 gene, at the same time for one or more of the genes chosen from the group consisting of the pck gene which codes for phosphoenol pyruvate carboxykinase (DE 199 50 409.1, DSM 13047), the pgi gene which codes for glucose 6-phosphate isomerase (U.S. Ser. 09/396,478, DSM 12969), the poxB gene which codes for pyruvate oxidase (DE:1995 1975.7, DSM 13114)

to be attenuated.

Thus, for example, for the production of L-valine at the same time the ilvBN gene which codes for acetohydroxy-acid synthase (Keilhauer et al., (1993) Journal of Bacteriology 175: 5595–5603), or at the same time the ilvD gene which codes for dihydroxy-acid dehydratase (Sahm and Eggeling (1999) Applied and Environmental Microbiology 65: 1973–1979), or at the same time the mqo gene which codes for malate-:quinone oxidoreductase (Molenaar et al., European Journal of Biochemistry 254, 395–403 (1998))

can be over-expressed.

In addition to attenuation of the lysR3 gene it may furthermore be advantageous, for the production of amino acids, in particular L-lysine and L-valine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids, in particular L-lysine and L-valine. A summary of known culture methods are [sic] described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by anion exchange chromatography with subsequent ninhydrin derivatization, or it can be carried out by reversed phase HPLC, for example as described by Lindroth et al. (Analytical Chemistry (1979) 51: 1167–1174).

The following microorganism has been deposited at the Deutsche Sammlung fur Mikroorganismen und Zellkulturen (DSMZ=German Collection of Microorganisms and Cell Cultures, Braunschweig, Germany) in accordance with the Budapest Treaty:

*Escherichia coli* strain TOP10F/pCR2.1lysR3int as DSM 13618.

The process according to the invention is used for the fermentative preparation of amino acids, in particular L-lysine and L-valine.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbour Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

EXAMPLE 1
Preparation of a Genomic Cosmid Gene Library from *C. glutamicum* ATCC 13032

Chromosomal DNA from *C. glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCosl (Wahl et al., 1987, Proceedings of the National Academy of Sciences, USA 84:2160–2164), obtained from Stratagene (La Jolla, USA, Product Description SuperCosl Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Res. 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor), the cells being plated out on LB agar (Lennox, 1955, Virology, 1:190)+100 μg/ml ampicillin. After incubation overnight at 37° C., recombinant individual clones were selected.

EXAMPLE 2
Isolation and Sequencing of the lysR3 Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the *E. coli* strain DH5αMCR (Grant, 1990, Proceedings of the National Academy of Sciences, U.S.A., 87:4645–4649) and plated out on LB agar (Lennox, 1955, Virology, 1:190) with 50 μg/ml zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academies of Sciences, U.S.A., 74:5463–5467) with modifications according to Zimmermann et al. (1990, Nucleic Acids Research, 18:1067). The "RR dRhodamin Terminator Cycle Sequencing Kit" from PE Applied Biosystems(Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZerol derivatives were assembled to a continuous contig. The computer-assisted coding region analysis [sic] were prepared with the XNIP program (Staden, 1986, Nucleic Acids Research, 14:217–231). Further analyses were carried out with the "BLAST search program" (Altschul et al., 1997, Nucleic Acids Research, 25:3389–3402) against the non-redundant databank of the "National Center for Biotechnology Information" (NCBI, Bethesda, Md., USA).

The resulting nucleotide sequence is shown in SEQ ID No. 1. Analysis of the nucleotide sequence showed an open reading frame of 633 base pairs, which was called the lysR3 gene. The lysR3 gene codes for a polypeptide of 210 amino acids.

EXAMPLE 3
Preparation of an Integration Vector for Integration Mutagenesis of the lysR3 Gene From the strain ATCC 13032, chromosomal DNA was isolated by the method of Eikmanns et al. (Microbiology 140: 1817–1828 (1994)). On the basis of the sequence of the lysR3 gene known for *C. glutamicum* from example 2, the following oligonucleotides were chosen for the polymerase chain reaction:

lysR3intA:
5'GAT GTG GTG TTG ATG GAT CT 3' (SEQ ID No. 4)
lysR3intB:
5'TCA ATT TCT CTG GCA CTG AG 3' (SEQ ID No. 5)

The primers shown were synthesized by MWG Biotech (Ebersberg, Germany) and the PCR reaction was carried out by the standard PCR method of Innis et al. (PCR protocols. A guide to methods and applications, 1990, Academic Press) with Pwo-Polymerase from Boehringer. With the aid of the polymerase chain reaction, an internal fragment of the lysR3 gene 323 bp in size was isolated, this being shown in SEQ ID No. 3.

The amplified DNA fragment was ligated with the TOPO TA Cloning Kit from Invitrogen Corporation (Carlsbad, Calif., USA; Catalogue Number K4500-01) in the vector pCR2.1-TOPO (Mead at al. (1991) Bio/Technology 9:657–663).

The E. coli strain TOP10F was then electroporated with the ligation batch (Hanahan, In: DNA cloning. A practical approach. Vol. I, IRL-Press, Oxford, Washington D.C., USA, 1985). Selection for plasmid-carrying cells was made by plating out the transformation batch on LB agar (Sambrook et al., Molecular Cloning: A Laboratory Manual. $2^{nd}$ Ed., Cold Spring Harbor Laboratory Press, Cold Spring Harbor, N.Y., 1989), which had been supplemented with 25 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1lysR3int.

EXAMPLE 4

Integration Mutagenesis of the lysR3 Gene in the Lysine Producer DSM 5715 and in the Valine Producer FERM BP-1763

The vector pCR2.1lysR3int mentioned in example 3 was electroporated by the electroporation method of Tauch et al.(FEMS Microbiological Letters, 123:343–347 (1994)) into Corynebacterium glutamicum DSM 5715 and Brevibacterium lactofermentum FERM BP-1763. The strain DSM 5715 is an AEC-resistant lysine producer. The strain FERM BP-1763 is a valine producer in need of isoleucine and methionine. The vector pCR2.1lysR3int cannot replicate independently in DSM 5715 or FERM BP-1763 and is retained in the cell only if it has integrated into the chromosome of DSM 5715 or FERM BP-1763. Selection of clones with pCR2.1lysR3int integrated into the chromosome was carried out by plating out the electroporation batch on LB agar (Sambrook et al., Molecular Cloning: A Laboratory Manual. $2^{nd}$ Ed., Cold Spring Harbor Laboratory Press, Cold Spring Harbor, N.Y.), which had been supplemented with 15 mg/l kanamycin.

For detection of the integration, the lysR3int fragment was labelled with the Dig hybridization kit from Boehringer by the method of "The DIG System Users Guide for Filter Hybridization" of Boehringer Mannheim GmbH (Mannheim, Germany, 1993). Chromosomal DNA of a potential integrant was isolated by the method of Eikmanns et al. (Microbiology 140: 1817–1828 (1994)) and in each case cleaved with the restriction enzymes SalI, SacI and HindIII. The fragments formed were separated by agarose gel electrophoresis and hybridized at 68° C. with the Dig hybrization [sic] kit from Boehringer. The plasmid pCR2.1lysR3int mentioned in example 3 had been inserted into the chromosome of DSM5715 and FERM BP-1763 within the chromosomal lysR3 gene. The strains were called DSM5715::pCR2.1lysR3int and FERM BP-1763::pCR2.1lysR3int.

EXAMPLE 5

Preparation of L-lysine and L-valine

The C. glutamicum and B. lactofermentum strains DSM5715::pCR2.1lysR3int and FERM BP-1763::pCR2.1lysR3int obtained in example 4 were cultured in a nutrient medium suitable for the production of L-lysine and L-valine and the L-lysine and L-valine content in the culture supernatant was determined.

For this, the strains were first incubated on an agar plate with the corresponding antibiotic (brain-heart agar with kanamycin (25 mg/l) for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to this. The preculture was incubated for 24 hours at 33° C. at 240 rpm on a shaking machine. A main culture was seeded from this preculture such that the initial OD (660 nm) of the main culture was 0.1 OD. Medium MM was used for the main culture.

| Medium MM | |
|---|---|
| CSL (corn steep liquor) | 5 g/l |
| MOPS | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| $CaCO_3$ | 25 g/l |

The CSL, MOPS and the salt solution are brought to pH 7 with aqueous ammonia and autoclaved. The sterile substrate and vitamin solutions are then added, as well as the $CaCO_3$ autoclaved in the dry state. For culturing of DSM 5715, 0.1 g/l leucine was additionally added to the medium. For culturing of FERM BP-1763, 0.1 g/l isoleucine and 0.1 g/l methionine were additionally added to the medium. Culturing is carried out in a 10 ml volume in a 100 ml conical flask with baffles. Kanamycin (25 mg/l) was added.

Culturing was carried out at 33° C. and 80% atmospheric humidity.

After 72 hours, the OD was determined at a measurement wavelength of 660 nm with a Biomek 1000 (Beckmann Instruments GmbH, Munich). The amount of L-lysine and of L-valine formed was determined with an amino acid analyzer from Eppendorf-BioTronik (Hamburg, Germany) by ion exchange chromatography and post-column derivatization with ninhydrin detection.

The results of the experiment are shown in tables 1 and 2.

TABLE 1

| Strain | OD (660) | Lysine HCl g/2 |
|---|---|---|
| DSM5715 | 7.5 | 13.01 |
| DSM5715::pCR2.1lysR3int | 7.6 | 15.04 |

TABLE 2

| Strain | OD (660) | Valine g/l |
|---|---|---|
| FERM BP-1763 | 12.1 | 7.49 |
| FERM BP-1763::pCR2.1lysR3int | 12.5 | 8.67 |

The abbreviations and designations used have the following meaning.

| KmR: | Kanamycin resistance gene |
|---|---|
| EcoRI: | cleavage site of the restriction enzyme EcoRI |
| lysR3int: | Internal fragment of the lysR3 gene |
| ColE1 ori: | Replication origin of the plasmid ColE1 |

Obviously, numerous modifications and variations on the present invention are possible in light of the above teachings. It is therefore to be understood that within the scope of the appended claims, the invention may be practiced otherwise than as specifically described herein.

What is claimed is:

1. A process for producing L-amino acids comprising culturing a bacterial cell in a medium suitable for producing L-amino acids, wherein said bacterial cell comprises an attenuated lysR3 gene, wherein the lysR3 gene prior to being attenuated comprises SEQ ID NO: 1, or a polynucleotide which hybridizes under stringent conditions to the full complement of SEQ ID NO:1 and encodes a protein with LysR3 transcriptional regulatory activity, wherein the stringent conditions comprise washing in 0.5×SSC at a temperature of 68° C.; and recovering the produced L-amino acid.

2. The process of claim 1, wherein said bacterial cell is a *Coryneform bacterium* or *Brevibacterium*.

3. The process of claim 1, wherein said bacterial cell is selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum,* and *Brevibacterium divaricatum*.

4. The process of claim 1, wherein said bacterial cell is selected from the group consisting of *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium flavum* ATCC14067, *Brevibacterium lactofermenium* ATCC13869, and *Brevibacterium divaricatum* ATCC14020.

5. The process of claim 1, wherein said lysR3 gene prior to being attenuated comprises the polynucleotide sequence of SEQ ID NO:1.

6. The process of claim 1, attenuated lysR3 gene comprises the polynucleotide sequence of SEQ ID NO:3.

7. The process of claim 1, wherein said L-amino acid is L-lysine.

8. The process of claim 1, wherein said L-amino acid is L-valine.

9. The process of claim 7, wherein said bacteria further comprises at least one gene which is overexpressed, wherein said gene is selected from the group consisting of dapA, eno, zwf, pyc, and lysE.

10. The process of claim 7, wherein said bacteria further comprises at least one gene whose expression is attenuated, wherein said gene is selected from the group consisting of pck, pgi, and poxB.

11. The process of claim 1, wherein said bacteria further comprises at least one gene which is overexpressed, wherein said gene is selected from the group consisting of ilvBN, ilvD and mqo.

12. The process of claim 1, wherein said lysR3 gene prior to being attenuated comprises a polynucleotide encoding a polypeptide comprising the amino acid sequence of SEQ ID NO:2.

* * * * *